United States Patent [19]

Burdeska et al.

[11] Patent Number: 4,780,558
[45] Date of Patent: Oct. 25, 1988

[54] SULFONE COMPOUNDS

[75] Inventors: Kurt Burdeska; Kurt Weber, both of Basel, Switzerland; Dieter Reinehr, Kandern, Fed. Rep. of Germany

[73] Assignee: Ciba-Geigy Corporation, Ardsley, N.Y.

[21] Appl. No.: 827,117

[22] Filed: Feb. 7, 1986

[30] Foreign Application Priority Data

Feb. 15, 1985 [CH] Switzerland .................. 730/85

[51] Int. Cl.⁴ .................. C07C 121/60; C07C 147/107
[52] U.S. Cl. .................. 558/401; 560/11
[58] Field of Search .................. 558/401; 560/11

[56] References Cited

U.S. PATENT DOCUMENTS 4,108,887  8/1978  Fleck et al. .................. 260/465 H
4,196,229  4/1980  Fleck et al. .................. 260/465 H
4,440,694  4/1984  Bellus et al. .................. 558/401

FOREIGN PATENT DOCUMENTS 189259  8/1986  Japan .

OTHER PUBLICATIONS

Gilman et al., "Organic Chemistry," vol. I, Second Edition, pp. 874–875.

Primary Examiner—Anton H. Sutto
Attorney, Agent, or Firm—Kevin T. Mansfield; Edward McC. Roberts

[57] ABSTRACT

The invention relates to novel sulfone compounds of formula I

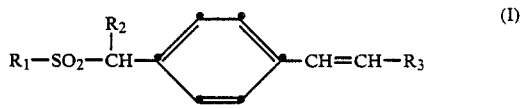

(I)

wherein
$R_1$ is an unsubstituted or substituted phenyl or naphthyl radical,
$R_2$ is hydrogen or the radical of the formula

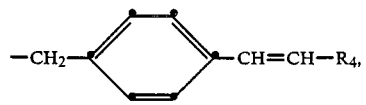

$R_3$ and $R_4$ are —CN or —COOR$_5$, in which $R_5$ is $C_1$–$C_4$alkyl, with the proviso that, if $R_2$ is the radical of the formula

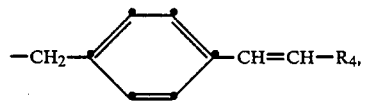

$R_3$ and $R_4$ in formula I may be identical or different.

The compounds of the invention are valuable intermediates for the preparation of fluorescent whitening agents of the stilbene series.

5 Claims, No Drawings

SULFONE COMPOUNDS

The invention relates to novel sulfone compounds, to a process for the preparation thereof, to the use thereof as intermediates for the preparation of fluorescent whitening agents, and to novel asymmetrically substituted stilbene compounds.

The novel sulfone compounds are of formula I

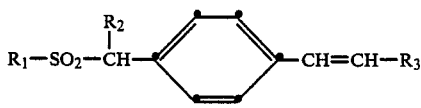

(I)

wherein $R_1$ is an unsubstituted or substituted phenyl or naphthyl radical, $R_2$ is hydrogen or the radical of the formula

$R_3$ and $R_4$ are —CN or —COOR$_5$, in which $R_5$ is $C_1$-$C_4$alkyl, with the proviso that, if $R_2$ is the radical of the formula

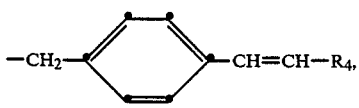

then $R_3$ and $R_4$ in formula I may be identical or different.

If $R_1$ is a substituted phenyl or naphthyl radical, then substituents are for example: halogen such as fluorine, chlorine or bromine; $C_1$-$C_4$alkyl (branched and unbranched) such as methyl, ethyl, n-propyl and isopropyl; as well as $NO_2$ and phenyl.

In the preferred compounds of formula I, $R_1$ is an unsubstituted or substituted phenyl radical, in particular a phenyl radical which is substituted by $C_1$-$C_4$alkyl, preferably methyl.

In the preferred compounds, $R_2$ is the radical of the formula

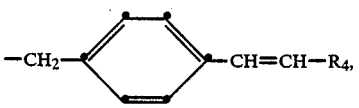

$R_4$ as a —COOR$_5$ group is preferably one of the following groups: —COOCH$_3$, —COOC$_2$H$_5$, —COOC$_3$H$_7$(n) and —COOC$_4$H$_9$(n). In preferred compounds, $R_4$ is —CN.

If $R_2$ is the grouping

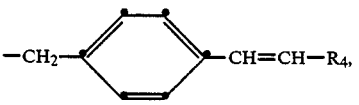

then the two substituents $R_3$ and $R_4$ according to formula I, within the scope of the definition, may be identical (e.g. each of $R_3$ and $R_4$ is —CN) or different (e.g. $R_3$ is —CN and $R_4$ is the —COOR$_5$ group).

The novel sulfone compounds of formula I, wherein $R_2$ is the group of the formula

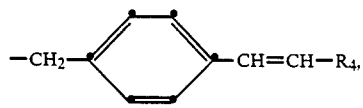

are in particular valuable intermediates for obtaining fluorescent whitening agents of the stilbene series. Those compounds of formula I, wherein $R_2$ is hydrogen, are used in particular for the preparation of compounds of formula I, wherein $R_2$ is the group of the formula

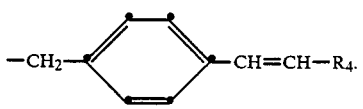

The sulfone compounds of formula I are prepared e.g. by reacting a cinnamic acid derivative of formula II

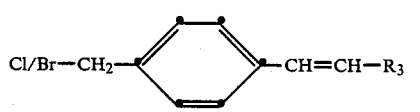

(II)

wherein $R_3$ is as defined above, with the sodium salt of the benzenesulfinic or naphthalenesulfinic acid of the formula $R_1$—SO$_2$Na (III) in organic, preferably alkaline, medium to give a compound of formula Ia

(Ia)

and, if desired, allowing said compound of formula Ia to react with one further mole of an identical or different cinnamic acid derivative of formula IV

(IV)

The reaction of the cinnamic acid derivative of formula II with the compound of formula III is carried out in organic medium, e.g. in dimethylformamide, dimethyl sulfoxide or tetrahydrofuran, preferably in alcoholic medium under heat. Suitable alcohols are for example: methanol, ethanol, propanol, isopropanol, butanols, glycols and glycol ethers.

The compounds of formulae II, III and IV are known and can be obtained in known manner. Examples of suitable cinnamic acid derivatives of formula II or IV are:

4-bromomethylcinnamonitrile,
4-chloromethylcinnamonitrile,
methyl 4-bromomethylcinnamate, and ethyl 4-bromomethylcinnamate.

Examples of starting compounds of formula III are:
benzenesulfinic acid (Na salt),
4-methylbenzenesulfinic acid (Na salt),
4-chlorobenzenesulfinic acid (Na salt), and
β-naphthylsulfinic acid (Na salt).

Compounds of formula I wherein $R_2$ is hydrogen (formula Ia) are obtained in this manner. Said compounds are used for preparing compounds of formula I, wherein $R_2$ is the group of the formula

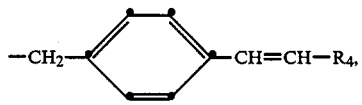

by reacting the compounds of formula Ia with one further mole of a cinnamic acid derivative of formula IV. This reaction is carried out with the aid of a base (e.g. NaOH) in an organic solvent. It is preferred to use those solvents which are suitable for a phase transfer reaction, e.g. methylene chloride or chlorobenzene; mixtures of such solvents e.g. with dimethylformamide or dimethyl sulfoxide may also be used. If necessary, the reaction is carried out under phase transfer conditions (with the aid of a phase transfer catalyst such as tetrabutylammonium bromide, butyltriethylammonium bromine or chloride, benzyltributylammonium bromide or chloride).

The novel compounds of formula I, wherein $R_2$ is the group of the formula

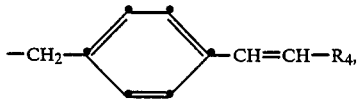

are used for the preparation of divinylstilbene compounds including, as novel compounds, the asymmetrically substituted 4,4'-divinylstilbene compounds of the formula

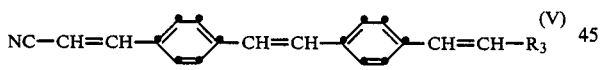 (V)

wherein $R_3$ is —COOR$_5$, in which $R_5$ is $C_1$-$C_4$alkyl.

Said stilbene compounds are conveniently obtained by dissolving or suspending the above compounds of formula I, wherein $R_2$ is the group of the formula

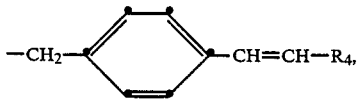

in water or in an organic solvent (e.g. lower alcohols such as methanol, ethanol, propanol, isopropanol or butanol, glycols, glycol monoalkyl ethers, polyglycol alkyl ethers, pyridine, N-methylpyrridone, aromatic hydrocarbons and, in particular, dimethylformamide or dimethyl sulfoxide) or a mixture thereof, adding a base to the resultant solution or suspension and heating to a temperature in the range from about 40° to 150° C.

Suitable bases are both inorganic and organic bases such as alkalis, alcoholates or amines, e.g. NaOH, Na$_2$CO$_3$, KOH, K$_2$CO$_3$, LiOH, CaCO$_3$, triethylamine and pyridine.

The stilbene compounds prepared from the novel sulfone compounds are suitable fluorescent whitening agents for polyester fibres.

The invention is illustrated in more detail by the following non-limitative Examples.

EXAMPLE 1

44.4 g of 4-bromomethylcinnamonitrile together with 36.11 g of the sodium salt of benzenesulfinic acid and 350 ml of ethanol are boiled for 3½ hours. The product, which precipitates after the mixture has cooled to room temperature, is isolated by filtration, washed with ethanol and then with water and dried in vacuo at 80° C., affording 52 g of the product of the formula

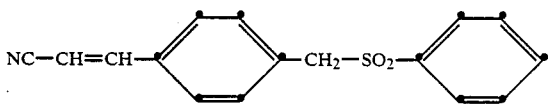

with a melting point of 181°–182° C.

By following the same procedure but using 35.53 g of 4-chloromethylcinnamonitrile (melting point: 85°–86° C.) in place of 44.4 g of 4-bromomethylcinnamonitrile, 4-cyanovinylbenzylsulfone is obtained in a yield of 87% of theory.

The compounds listed in Table 1 can be prepared by following a procedure analogous to that of Example 1:

TABLE 1

| Example | R$_1$ | Melting point (°C.) |
|---|---|---|
| 2 | —⌬—CH$_3$ | 179–181° |
| 3 | —⌬—Cl | 218–219° |
| 4 | —⌬(Cl)—Cl | 219–220° |
| 5 | naphthyl | 193–194° |

TABLE 1-continued

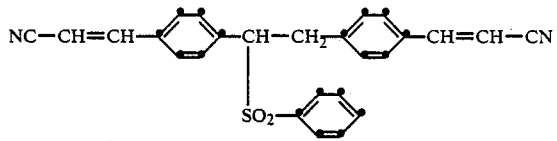

| Example | R₁ | Melting point (°C.) |
|---|---|---|
| 6 | 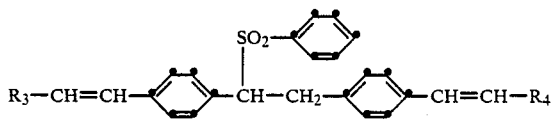 NO₂ | 187–188° |

EXAMPLE 7

38.26 g of methyl 4-bromomethylcinnamate (melting point: 59°–60° C.) together with 27.9 g of the sodium salt of benzenesulfinic acid and 200 ml of ethanol are boiled under reflux for 3 hours. After the mixture has cooled to room temperature, the precipitated product is isolated by filtration, washed with ethanol and then with water and dried, affording 43.4 g (91.6%) of the compound of the formula

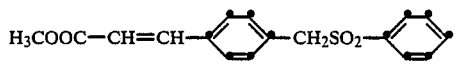

with a melting point of 162°–163° C.

By following the same procedure but using equivalent amounts of ethyl 4-bromomethylcinnamate (melting point: 45°–47° C.) in place of methyl 4-bromomethylcinnamate, the compound of the formula

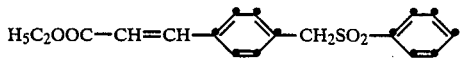

with a melting point of 137°–138° C. is obtained.

By reacting methyl 4-bromomethylcinnamate with the sodium salt of 4-chlorobenzenesulfinic acid, the compound

with a melting point of 227°–228° C. is obtained.

EXAMPLE 8

28.33 g of 4-cyanovinylbenzylphenylsulfone, prepared in accordance with Example 1, and 22.2 g of bromomethylcinnamonitrile are dissolved in a mixture of 200 ml of methylene chloride and 40 ml of dimethyl sulfoxide. After the addition of 2 g of tetrabutylammonium bromide and 14 g of a 30% aqueous solution of NaOH, the mixture is heated, with fast stirring, to reflux temperature and then held at boiling point for 12 hours. After 5 hours, a further 0.5 g of tetrabutylammonium bromide is added to the reaction mixture. When the reaction is complete, the methylene chloride is distilled off in vacuo, and 200 ml of water are added to the residue. The product obtained is isolated by filtration, finely ground with water, once more isolated by filtration, washed with water and then with ethanol and dried in vacuo at 80° C., affording 42.1 g (97.1% of theory) of the product of the formula

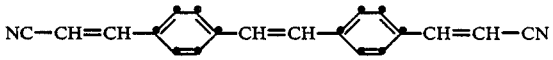

with a melting point of 200°–202° C.

The compounds listed in Table 2 can be prepared by following a procedure analogous to that of Example 8:

TABLE 2

$$R_3-CH=CH-\text{\char{[}Ar\char{]}}-CH-CH_2-\text{\char{[}Ar\char{]}}-CH=CH-R_4$$
(with SO₂—Ph substituent)

| Example | R₃ | R₄ | Melting point (°C.) |
|---|---|---|---|
| 9 | —CN | —COOCH₃ | 156–157° |
| 10 | —CN | —COOC₂H₅ | 166–168° |
| 11 | H₃COOC | —COOCH₃ | 132–133° |
| 12 | H₅C₂OOC | —COOC₂H₅ | 140–141° |
| 13 | H₃COOC | —COOC₂H₅ | 135–136° |

EXAMPLE 14

21.22 g of the compound prepared in accordance with Example 8 are suspended in 140 ml of ethylene glycol and, after the addition of 5.18 g of anhydrous potassium carbonate, the suspension is heated, with good stirring, for 4 hours at 100°–105° C. The reaction mixture is then allowed to cool to room temperature, and 6 ml of acetic acid are cautiously added. The resultant mixture is stirred for a further 20 minutes at room temperature and then filtered. The filtrate is washed in succession with methanol, water and methanol and dried in vacuo at 80° C., affording 14 g of the stilbene compound of the formula NC—CH=CH—[Ar]—CH=CH—[Ar]—CH=CH—CN in the form of pale green crystals with a melting point of 222°–225° C.

EXAMPLE 15

27.45 g of the compound prepared in accordance with Example 9 are dissolved in 90 ml of dimethylformamide, and 11 g of a 30% solution of sodium methylate are added to the solution over 30 minutes at room temperature. The mixture is subsequently stirred for a further 30 minutes at room temperature and, in order to complete the reaction, for a further hour at 40°–45° C. After the addition of 10 ml of methanol, the mixture is cooled to 5° C., the precipitated product of the formula

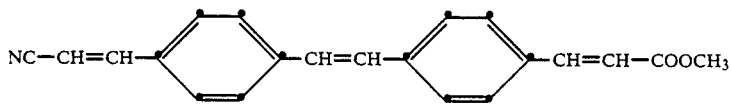

is isolated by filtration, washed with methanol and with water and dried in vacuo at 80° C. The yield is 13.7 g of greenish yellow crystals with a melting point of 183°–186° C.

EXAMPLE 16

By employing the compound of Example 10, the following compound is obtained:

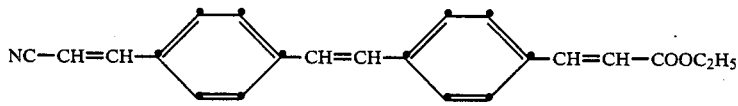

Melting point: 151°–153° C.

What is claimed is:

1. A sulfone compound of formula I

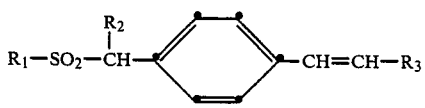 (I)

wherein
  $R_1$ is an unsubstituted or substituted phenyl or naphthyl radical,
  $R_2$ is a radical of the formula

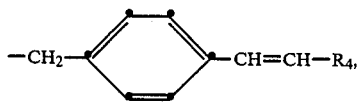

$R_3$ and $R_4$ are —CN or —COOR$_5$, in which $R_5$ is $C_1$–$C_4$alkyl, with the proviso that $R_3$ and $R_4$ in formula I may be identical or different.

2. A sulfone compound according to claim 1, wherein $R_1$ is an unsubstituted or substituted phenyl radical.

3. A sulfone compound according to claim 2, wherein $R_1$ is a phenyl radical which is unsubstituted or substituted by $C_1$–$C_4$alkyl.

4. A sulfone compound according to claim 1, wherein each of $R_3$ and $R_4$ is —CN.

5. A process for the preparation of a sulfone compound of formula I

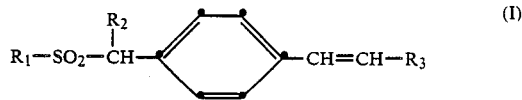 (I)

wherein
  $R_1$ is an unsubstituted or substituted phenyl or naphthyl radical,
  $R_2$ is a radical of the formula

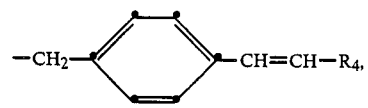

$R_3$ and $R_4$ are —CN or —COOR$_5$, in which $R_5$ is $C_1$–$C_4$alkyl, which process comprises heating a cinnamic acid derivative of formula II

 (II)

with the sodium salt of a benzenesulfinic or naphthalenesulfinic acid of the formula $R_1$—SO$_2$Na (III) in an organic solvent to give a compound of the formula Ia

 (Ia)

and heating said compound of formula Ia with one further mole of an identical or different cinnamic acid derivative of formula IV

 (IV)

with a base and an organic solvent.

* * * * *